United States Patent [19]
Fujii

[11] Patent Number: 5,468,364
[45] Date of Patent: Nov. 21, 1995

[54] BASE SEQUENCING APPARATUS

[75] Inventor: Hidehiko Fujii, Kyoto, Japan

[73] Assignee: Shimadzu Corporation, Japan

[21] Appl. No.: 65,065

[22] Filed: May 24, 1993

[30] Foreign Application Priority Data

May 29, 1992 [JP] Japan ..................................... 4-163507

[51] Int. Cl.$^6$ ......................... G01N 27/26; G01N 27/447
[52] U.S. Cl. ..................................... 204/299 R; 204/182.8
[58] Field of Search .............................. 204/299 R, 182.8

[56] References Cited

PUBLICATIONS

Robert E. Milofsky and Edward S. Yeung "Native Fluorescence Detection of Nucleic Acids and DNA Restriction Fragments in Capillary Electrophoresis" Analytical Chemistry (Jan. 1993) 153–157.

Norman J. Dovichi et al "Three DNA Sequencing Methods Using Capillary Gel Electrophoresis and Laser Induced–Fluorescence" Analytical Chemistry (Dec. 1991) 2835–2841.

Thomas T. Lee and Edward S. Yeung "High–sensitivity laser–induced fluorescence detection of native proteins in capillary electrophoresis" Journal of Chromatography 595 (1992) 319–325.

*Primary Examiner*—John Niebling
*Assistant Examiner*—John S. Starsiak, Jr.
*Attorney, Agent, or Firm*—Klima & Hopkins

[57] ABSTRACT

Disclosed herein is an on-line base sequencing apparatus, which is provided with electrophoresis tubes having a sheath flow part in each lower end thereof, which a sulfuric acid solution of pH 1.0 is continuously fed to form a sheath flow. The portions close to the outlets provided in the lower ends are irradiated with light which is close to 260 nm. In order to detect fluorescence components, each electrophoresis tube is provided with a detection system involving an interference filer for selecting that of 340 to 390 nm from the fluorescence components. Outputs of such four detection systems are successively identified, to determine base sequences.

10 Claims, 2 Drawing Sheets

BASE SEQUENCING APPARATUS

BACKGROUND OF THE INVENTION

1. Field of the Invention

The present invention relates to an on-line base sequencing apparatus which comprises a gel electrophoresis apparatus for electrophoresing nucleic acid fragments such as DNA fragments treated by the Sanger method through electrophoresis lanes provided for the respective types of end bases thereby determining the base sequences of nucleic acids from the order of elution.

2. Description of the Background Art

An on-line base sequencing apparatus detects labeled DNA fragments, which are treated by the Sanger method, in order of elution, for detecting the DNA fragments eluted from electrophoresis gels. While study has been performed by using labeling materials of radioisotopes, which have been used in an off-line method, the apparatus is increased in size with inconvenience in handling in this case. Thus, generally carried out are a method of using fluorescent labels (refer to Nature, 1986, Vol. 321, pp. 674–679) and a method of using stable isotope labels (refer to Japanese Patent Laying-Open Gazette No. 2-176552 (1990)).

In such a base sequencing method using no radio isotopes, it is necessary to partially label DNAs with fluorescent materials or isotopes in advance of pretreatment by the Sanger method. Depending on the labeling method (or materials or portions), however, the Sanger reaction itself is influenced, and it is impossible to use specific primers and other chemical materials which have been used in the method employing radioisotopes.

There has recently been reported an attempt for electrophoresing DNA fragments labeled with neither fluorescent materials nor isotopes through gel filled capillaries and irradiating the DNA fragments with ultraviolet rays during such electrophoresis to excite the same, for detecting the as-generated fluorescence (refer to Anal. Chem., Vol. 65, No. 2, pp. 153–157 (1993)). In this case, however, the background is increased due to fluorescence also generated from the gels, while it is difficult to detect the fluorescence generated from the DNA fragments since the gels absorb such fluorescence. Although the capillaries are strongly acidified or alkalified in order to increase fluorescence efficiency of the DNA fragments, the DNA fragments are disadvantageously decomposed when the same are electrophoresed through strongly acidic gels, for example, and it is impossible to maintain the states of the DNA fragments which have been prepared by the Sanger method for the respective end bases. In such electrophoresis using strongly acidified gel filled capillaries, therefore, it is impossible to determine base sequences of DNAs even if fluorescence from unlabeled DNA fragments can be detected in high sensitivity.

SUMMARY OF THE INVENTION

An object of the present invention is to eliminate necessity for labeling nucleic acid fragments with fluorescent materials or isotopes in an on-line base sequencing apparatus.

According to the present invention, nucleic acid fragments eluted from electrophoresis parts are guided under strong acid environment and irradiated with ultraviolet rays which are close to 260 nm to generate fluorescence components, which in turn are detected for determination of base sequences. The strong acid environment for receiving the eluted nucleic acid fragments is formed by an acid solution having a pH value of 0.1 to 3.0, preferably about 1.0.

The inventor have found that nucleic acid fragments placed under environment having a pH value of about 0.1 to 3.0 generate fluorescence components, the wavelength of which are in the vicinity of 340 to 390 nm, when the same are excited with an ultraviolet ray of wavelength of 220 to 320 nm, preferably close to 260 nm. The nucleic acid fragments are decomposed under the acid environment to form adenosine and guanosine, which in turn are excited with the ultraviolet rays of 220 to 320 nm, to generate fluorescence components.

Nucleic acid fragments pretreated by the Sanger method are separated by electrophoresis through polyacrylamide gels, to be eluted in order which is responsive to the sequences. The as-eluted nucleic acid fragments are placed under strong acid environment before the same are diffused, to form adenosine and guanosine. The as-formed adenosine and guanosine generate fluorescence components of 340 to 390 nm upon irradiation with light of 220 to 320 nm, so that the nucleic acid fragments are detected. Thus, it is possible to determine the base sequences of the nucleic acid fragments with no labeling.

According to the present invention, it is not necessary to label nucleic acid fragments to be subjected to base sequencing with fluorescent materials or isotopes, whereby the operation is extremely simplified.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
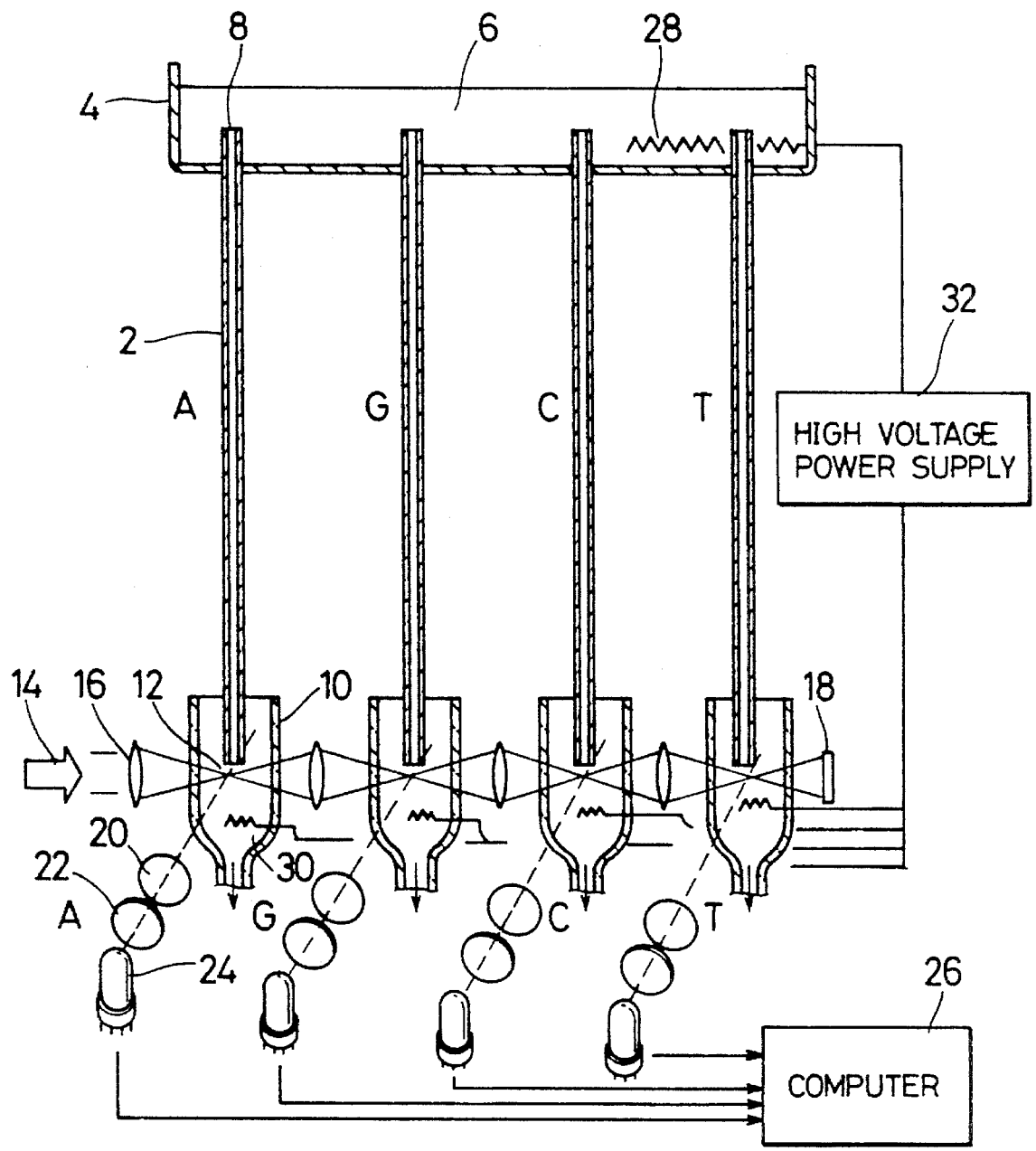
FIG. 1 is a schematic block diagram showing an embodiment of the present invention.

FIG. 1 schematically illustrates a base sequencing apparatus according to an embodiment of the present invention.

Electrophoresis tubes 2, which are formed by capillaries filled up with a polyacrylamide gel, are prepared for respective end bases of A (adenine), G (guanine), C (cytosine) and T (thymine) treated by the Sanger method. Upper ends of the electrophoresis tubes 2 are dipped in an electrolyte 6 contained in a cathode vessel 4, so that samples are introduced into openings provided in such upper ends. Each electrophoresis tube 2 is provided on a lower end thereof with a sheath flow part 10 for feeding a strong acid solution as a sheath flow, so that a sulfuric acid solution of pH 0.1 to 3.0, preferably 1.0 is continuously fed to the sheath flow part 10 to form a sheath flow in a portion 12 close to an outlet provided in the lower end of the electrophoresis tube 2. The sheath flow parts 10 are made of a material such as quartz glass, which transmits ultraviolet rays and does not emit fluorescence by excitation with the ultraviolet rays. Such technique for making a sheath flow on an end of a capillary electrophoresis tube is already known as described in Anal. Chem., Vol. 63, No. 24, pp. 2835–2841 (1991), for example.

In order to apply an electrophoresis voltage to the electrophoresis tubes 2, a cathode 28 is provided in the electrolyte 6 which is contained in the cathode vessel 4 while an anode 30 is provided in the sulfuric acid solution contained in each sheath flow part 10 provided in the lower end of the electrophoresis tube 2, so that a high voltage power supply 32 applies an electrophoresis voltage across the cathode 28 and the anodes 30.

The portion 12 of each electrophoresis tube 2 close to the lower outlet is in the sheath flow, to be irradiated with excitation light 14 of a wavelength of 220 to 320 nm, preferably close to 260 nm, emitted from an ultraviolet light source, which is condensed by lenses 16. The portions 12 of the four electrophoresis tubes 2 are aligned with each other so that the excitation light 14 transmitted through the portion 12 of the first electrophoresis tube 2 is successively applied to the portion 12 of the second, third and fourth electrophoresis tubes 2. In order to improve irradiation efficiency, the lenses 16 are adapted to successively condense the as-applied excitation light 14 so that the portions 12 are successively irradiated with this light. Thus, the portions 12 close to the lower ends of the four electrophoresis tubes 2 are entirely irradiated by the excitation light 14 emitted from a single light source. A light trap 18 is provided to receive the excitation light 14 transmitted through the portion 12 of the final electrophoresis tube 2. The ultraviolet light source can be prepared from an argon ion laser of 275.4 nm or a KrF laser of 248 nm, XeCl laser of 308 nm, glass YAG laser of 263 to 266 nm or second harmonics of various visible lasers, for example.

In order to extract and detect fluorescence components in a direction perpendicular to that of irradiation with the excitation light 14, each electrophoresis tube 2 is provided on the lower end portion thereof with a detection system. Each detection system is formed by a lens 20 for condensing the fluorescence components, an interference filter 22 for selecting that of 340 to 390 nm from the fluorescence components condensed and extracted by the lens 20, and a photomultiplier 24 for detecting the fluorescence components selected by the interference filter 22.

The fluorescence components detected by the photomultipliers 24 are converted to electric signals and further converted to digital signals by A-D converters (not shown), to be thereafter incorporated in a computer 26. Such detection systems are provided for the respective four electrophoresis tubes 2 in which DNA fragments terminating in the end bases A, G, C and T are introduced. Thus, it is possible to determine the base sequences by successively identifying the outputs of the four photomultipliers 24.

Figure 2:
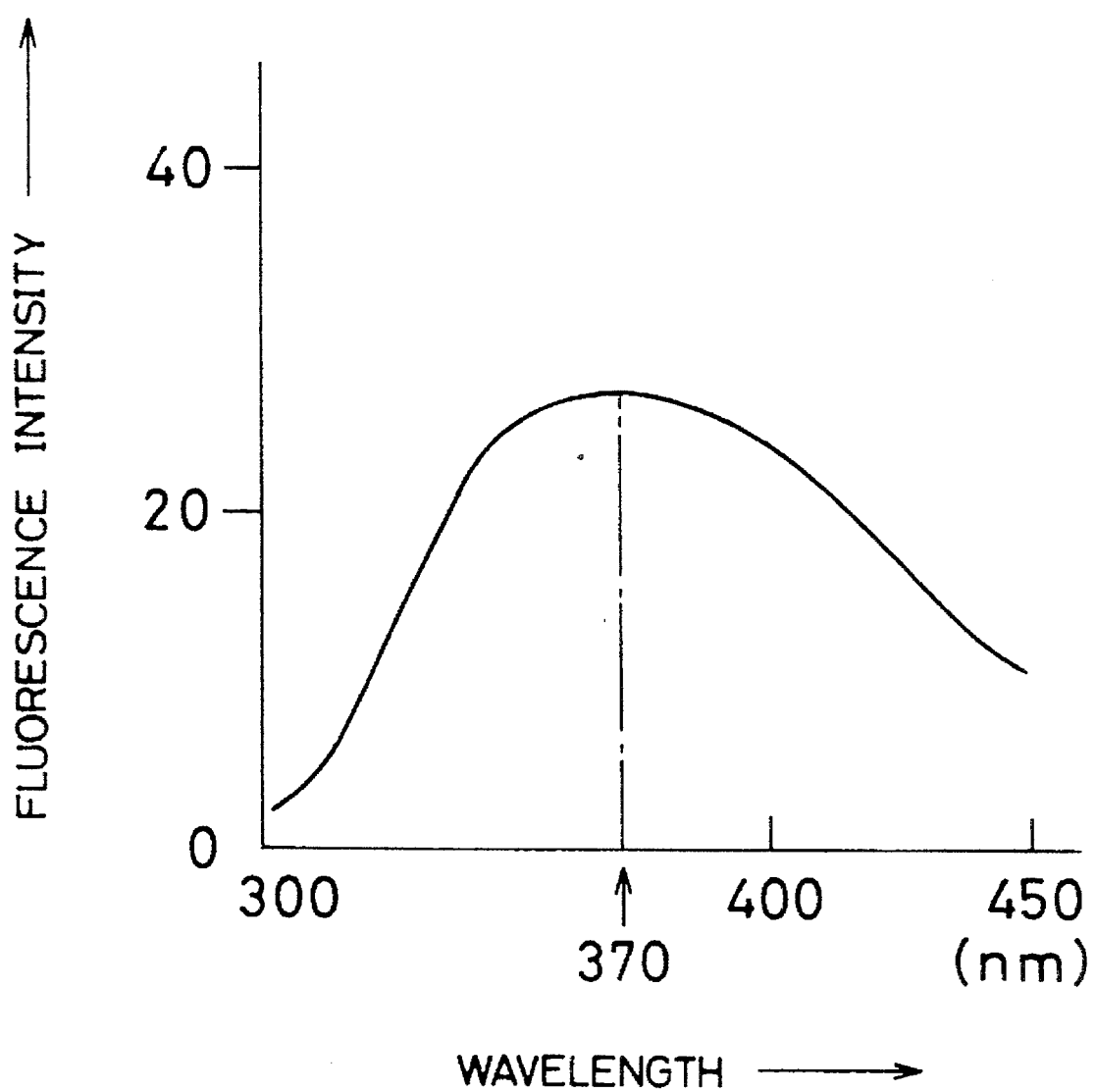
FIG. 2 illustrates a fluorescence spectrum of DNA at pH 1.0.

FIG. 2 illustrates a fluorescence spectrum of a DNA under environment of pH 1.0, with an excitation wavelength of 265 nm. This fluorescence spectrum was measured with a spectrophotometer (RF-540 by Shimadzu Corporation). As understood from FIG. 2, the spectrum is widely distributed around wavelengths of 340 to 390 nm while the peak wavelength is at 370 nm.

The operation of the embodiment shown in FIG. 1 is now described.

A DNA fragment eluted from the outlet provided on the lower end of the electrophoresis tube 2 for the end base A is immediately placed under the environment of pH 1.0 for example, by the sheath flow. This DNA fragment generates fluorescence of wavelength close to 340 to 390 nm since the portion 12 close to the outlet on the lower end of the electrophoresis tube 2 is irradiated with ultraviolet light of 260 nm for example. This fluorescence is detected by the photomultiplier 24 of the detection system provided for this electrophoresis tube 2. This also applies to the electrophoresis tubes 2 for the remaining end bases G, C and T. Namely, DNA fragments eluted from the respective electrophoresis tubes 2 are detected by fluorescence components generated by the same, so that the computer 26 determines the base sequences.

The present invention is also applicable to an electrophoresis apparatus employing a slab gel.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A base sequencing apparatus provided with a gel electrophoresis apparatus for electrophoresing nucleic acid fragments treated by the Sanger method through electrophoresis lanes provided for respective types of end bases for determining base sequences of nucleic acids from order of elution, said base sequencing apparatus comprising:

means for guiding the nucleic acid fragments being eluted from the electrophoresis lanes under a strong acid environment;

an ultraviolet ray irradiation means for irradiating the nucleic acid fragments under said strong acid environment with ultraviolet rays; and a fluorescence detection means for detecting fluorescence components generated from irradiated nucleic acid fragments.

2. A base sequencing apparatus in accordance with claim 1, wherein said ultraviolet ray irradiation means is adapted to emit ultraviolet rays of 220 to 320 mn, and said fluorescence detection means is adapted to detect fluorescence components of 340 to 390 nm.

3. A base sequencing apparatus in accordance with claim 1, wherein said strong acid environment for receiving said nucleic acid fragments being eluted from said gel electrophoresis apparatus is formed by an acid solution having a pH value of 0.1 to 3.0.

4. A base sequencing apparatus in accordance with claim 3, wherein the pH value of said strong acid environment is about 1.0.

5. A base sequencing apparatus in accordance with claim 1, wherein said gel electrophoresis apparatus comprises capillary electrophoresis tubes being arranged for respective said end bases of said nucleic acid fragments and having openings in upper ends for serving as portions for receiving said fragments, said capillary electrophoresis tubes being filled up with a polyacrylamide gel, each capillary electrophoresis tube is provided on lower end portion thereof with a sheath flow part for feeding a strong acid solution in a form of a sheath flow as the means for guiding said nucleic acid fragments being eluted from said capillary electrophoresis tube under said strong acid environment, and said upper ends of said capillary electrophoresis tubes are dipped in an electrolyte being contained in a cathode vessel storing a cathode while each sheath flow part contains an anode being dipped in said strong acid solution so that an electrophoresis voltage is applied across said cathode and said anode.

6. A base sequencing apparatus in accordance with claim 5, wherein said strong acid solution is a sulfuric acid solution having a pH value of 0.1 to 3.0.

7. A base sequencing apparatus in accordance with claim 6, wherein the pH value of said sulfuric acid solution is about 1.0.

8. A base sequencing apparatus in accordance with claim 5, wherein said lower ends of at least a set of four types of said capillary electrophoresis tubes being responsive to base ends are aligned with each other, said sheath flow parts are made of ultraviolet ray transmitting materials, said ultraviolet ray irradiation means guides excitation light from an ultraviolet light source to irradiate said lower ends of at least a set of capillary electrophoresis tubes in common, and said fluorescence detection means are so provided for respective said capillary electrophoresis tubes as to extract fluorescence components in a direction perpendicular to that of irradiation of said excitation light from said lower ends of said capillary electrophoresis tubes.

9. A base sequencing apparatus in accordance with claim 8, wherein said ultraviolet ray irradiation means includes:

a first condenser lens being provided in the exterior of said sheath flow part of the first one of said capillary electrophoresis tubes for condensing said excitation light being emitted from said ultraviolet light source and irradiating said lower end of said first capillary electrophoresis tube with said light through said sheath flow part, and second condenser lenses being provided between said sheath flow parts for condensing said excitation light being transmitted through precedent said sheath flow parts and irradiating said lower ends of subsequent said sheath flow parts with said excitation light.

10. A base sequencing apparatus in accordance with claim 8, wherein said fluorescence detection means includes:

condenser lenses for condensing light received from said lower ends of said capillary electrophoresis tubes, interference filters for selecting fluorescence components of 340 to 390 nm from said light condensed by said condenser lenses, and photomultipliers for detecting said fluorescence components being selected by said interference filters.

* * * * *